United States Patent
Kawano

(10) Patent No.: US 7,313,971 B2
(45) Date of Patent: Jan. 1, 2008

(54) MATERIAL TESTING MACHINE

(75) Inventor: Toshiyuki Kawano, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 162 days.

(21) Appl. No.: 11/305,023

(22) Filed: Dec. 19, 2005

(65) Prior Publication Data

US 2006/0162463 A1 Jul. 27, 2006

(30) Foreign Application Priority Data

Jan. 26, 2005 (JP) ............................. 2005-018740

(51) Int. Cl.
*G01N 3/00* (2006.01)

(52) U.S. Cl. .......................................... 73/794; 73/788

(58) Field of Classification Search .................. 73/794, 73/788, 760, 795–798

See application file for complete search history.

(56) References Cited

FOREIGN PATENT DOCUMENTS

JP            62014205 A    *   1/1987
JP            06123686 A    *   5/1994

* cited by examiner

*Primary Examiner*—Michael Cygan
*Assistant Examiner*—Punam Patel
(74) *Attorney, Agent, or Firm*—Manabu Kanesaka

(57) ABSTRACT

A material testing machine includes a load mechanism for applying a load to a test piece, and a plurality of detectors for detecting physical values associated with the applied load. An A/D converter receives the output measurement data of each of the detected physical values, and digitalizes the received output data. The A/D converter has multiple channels, and can select use/nonuse of each of the multiple channels based on an external selection signal. Since the detecting rate and/or the detecting accuracy are inversely proportional to the number of multiple channels in use at one time, the machine enables a user to prioritize between the number of channels in use, the detecting rate, and the detecting accuracy.

8 Claims, 2 Drawing Sheets

MATERIAL TESTING MACHINE

BACKGROUND OF THE INVENTION AND RELATED ART STATEMENT

The present invention relates to a material testing machine. More specifically, the invention relates to a material testing machine that digitalizes the detection output of the test force which acts on a test piece or the amount of the deformation (extension) of the test piece by an A/D converter, and obtains these measurement data.

Generally, in a material testing machine, the load is added to the test piece by driving a load mechanism. The test force exerted on the test piece by the load is constantly detected by a load cell, or, the deformation of the test piece, for example, the extension, is constantly detected by an extensometer. From the results of the constant detection, the characteristics of the test piece are examined, or the detection values selected as the amount of the control of these detection values are fed back to a target value signal. Accordingly, the load mechanism is driven and controlled.

Usually, in this kind of material testing machine, the detection output of the test force by the load cell, or the detection output of the extension by the extensometer is digitalized by the A/D converter after being amplified respectively by an amplifier. The detected output is used for various data processing as measurement data of the test force or extension, or the feedback controls (for example, refer to Japanese Patent Unexamined Publication No. 2002-357521 and Japanese Patent Unexamined Publication No. 2004-212172).

In a conventional material testing machine, the A/D converter is provided for every multiple detection output, or, an IC for A/D conversion with multiple channels is used. Also, a device using multiplexed multiple channels is used. However, in either case, the number of channels for the A/D conversion is preset to a certain number, and cannot be changed. Moreover, the sampling rate and accuracy of each A/D converter or each channel are individually constant, and never change.

However, in the above-mentioned conventional material testing machine, the number of channels for the A/D conversion which can be inputted as a device is fixed. As a result, for example, in a material testing machine with four channels for the A/D conversion, when only one channel is used, the other three channels do not contribute to the conversion at all so that the three channels are useless.

Accordingly, in the material testing machine with multiple channels for A/D conversion of the present invention, an object of the invention is to provide a material testing machine able to be set with the maximal resource according to the use condition of a user without wasting an unused channel.

Further objects and advantages of the invention will be apparent from the following description of the invention.

SUMMARY OF THE INVENTION

In order to attain the above-mentioned object, a material testing machine according to the present invention includes: a load mechanism for applying load to a test piece; and multiple detectors for detecting multiple physical values, including a test force acting on the test piece by the load and a deformation of the test piece, respectively. The material testing machine digitalizes an output from each above-mentioned detector by an A/D converter, and obtains measurement data for each above-mentioned physical value.

The A/D converter is an A/D converter with multiple channels able to select use/nonuse of each channel by a selection signal from the outside. At the same time, in the A/D converter, the fewer the number of channels that are used, the better the sampling rate and/or accuracy. In a first embodiment of the invention, the material testing machine includes a selective means supplying the selection signal of the use/nonuse of the channel for the A/D converter.

In a second embodiment, the present invention includes multiple A/D converters, at least one optional output of each detector described hereinabove is input to channels of the multiple A/D converters in parallel, and the channel of one optional A/D converter among the multiple A/D converters is placed in a used condition.

The present invention includes a digital communication function by providing a delta-sigma type IC for the A/D conversion. Also, the present invention uses an A/D converter that is able to specify the number of the channels and sampling rate according to the content of communication. The present invention solves problems by using the above-mentioned functions effectively.

Specifically, in a delta-sigma type A/D converter, use/nonuse of each multiple channel can be specified by the digital communication, and the number of channels provided for the use, and the sampling rate, and/or the accuracy, are traded off. Such an IC for the A/D conversion is also used for a conventional material testing machine. However, in a conventional machine, the number of the channels, the sampling rate, and the accuracy are used with a fixed state primarily set.

The present invention actively utilizes the above-mentioned function, and provides a channel-selective means that supplies the selection signal of the channel using the above-mentioned A/D converter. As a result, only actually used channels among multiple numbers of channels can be in a used state, and other channels can be in a non-used state. Herewith, the number of the channels and the sampling rate can be dynamically changed by a user side so that the user can choose which to prioritize between the number of channels, sampling rate, or accuracy.

Also, according to the second embodiment, if the invention includes the above-mentioned multiple A/D converters, the output of one detector is input to the channels of the multiple A/D converters in parallel. If only one channel among the channels is in the used state, the above-mentioned function can be realized without changing a connection to the channel for the A/D conversion of the output of the detector.

According to the invention, in a material testing machine with the channels for the multiple A/D conversions, without wasting the channels which are not used, the priority sequence of the number of the used channels, sampling rate, and accuracy can be determined as chosen by the operator. The combination of the number of channels, the sampling rate, and the accuracy can be set optimally according to the use conditions such as the content of the test conducted by the user.

DETAILED DESCRIPTION OF THE PREFERRED EMBODIMENTS

Hereinafter, embodiments of the present invention will be explained with reference to the drawings.

Figure 1:
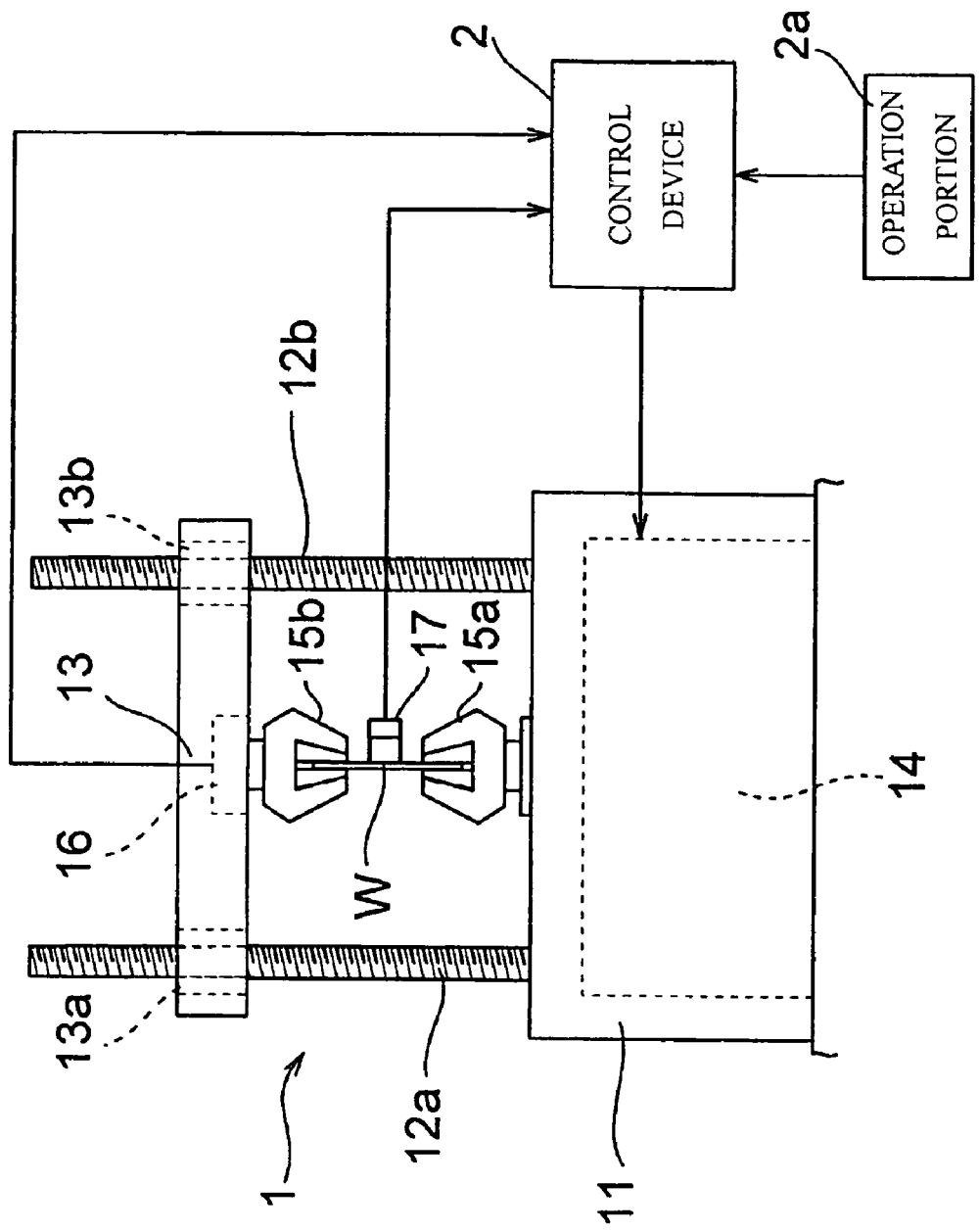
FIG. 1 is a structural view of an embodiment of the present invention and includes a schematic diagram showing a mechanical structure, and a block diagram showing a system structure.
Figure 2:
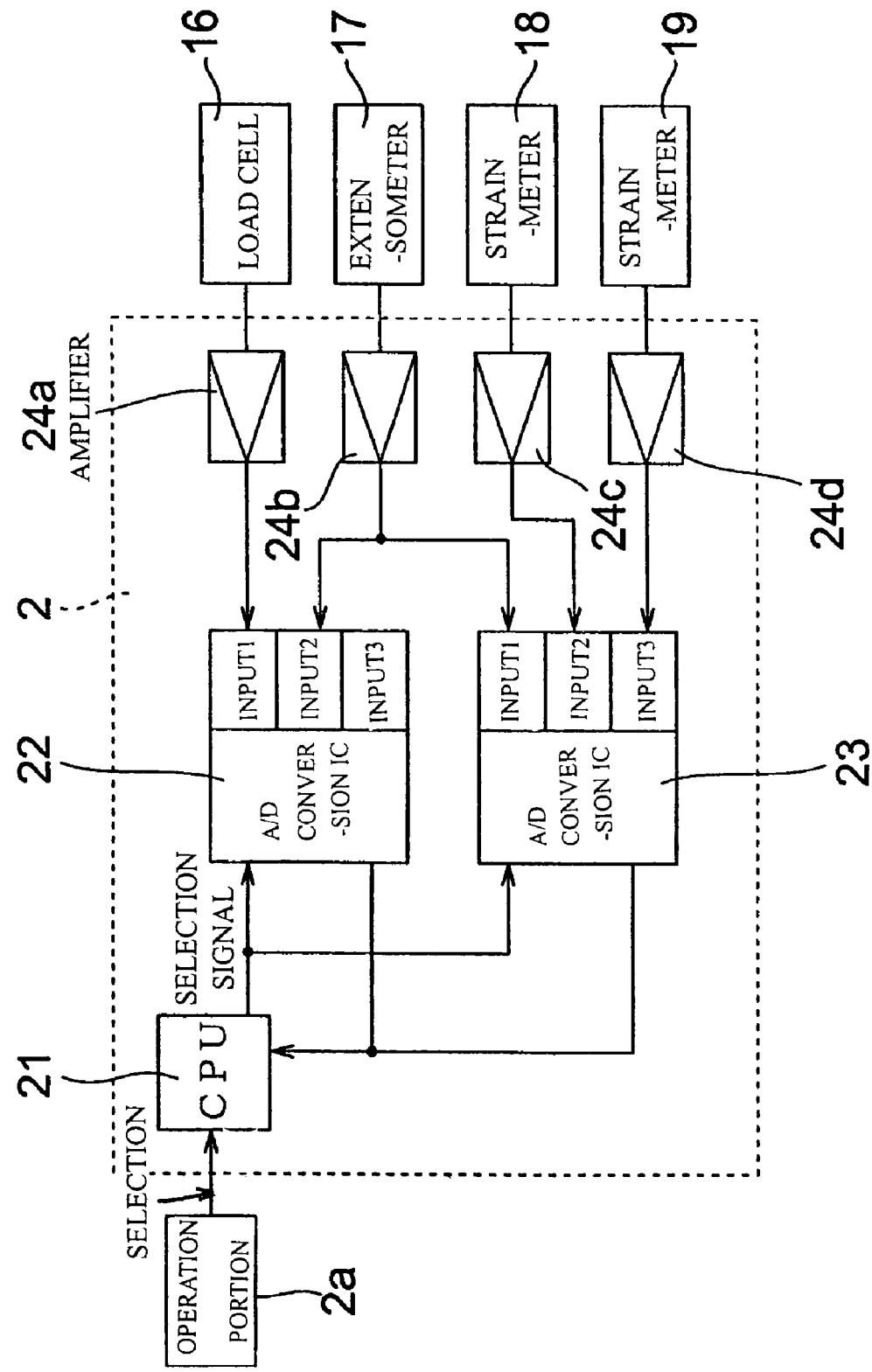
FIG. 2 is a block diagram showing the structure of components of a control device according to the embodiment of the present invention.

FIG. 1 is an overall structural view of the embodiment of the present invention and includes a schematic diagram showing a mechanical structure and a block diagram showing a system structure. FIG. 2 is a block diagram showing the structure of components of a control device 2.

In a testing machine main body 1, two screw poles 12a, 12b are placed to be freely rotatable on a table 11. Both end portions of a crosshead 13 are supported by each screw pole 12a, 12b through screw nuts 13a, 13b, and each screw pole 12a, 12b is rotary-driven by a driving device 14. Accordingly, the crosshead 13 approaches/departs relative to the table 11.

The testing machine main body 1 in FIG. 1 is set to conduct a tensile test. Grip portions 15a, 15b are respectively attached to the table 11 and crosshead 13 in such a way as being opposed to each other. The crosshead 13 is raised in a state wherein both end portions of a test piece W are gripped by the grip portions 15a, 15b. As a result, tensile load is applied to the test piece W.

The test force acting on the test piece W is detected by a load cell 16 placed between the crosshead 13 and upper side grip portion 15b. Also, the extension of the test piece W is detected by an extensometer 17 placed in the test piece W, and each detection output is taken in the control device 2 every second respectively.

The control device 2 houses two A/D conversion ICs 22, 23 and multiple amplifiers 24a-24d, besides CPU 21 and peripheral equipment (not shown in the figure) such as RAM, ROM, and so on. Outputs from the load cell 16 and extensometer 17 are digitalized by the A/D conversion IC 22 or 23 after being amplified by the amplifiers 24a-24b. The outputs are converted to test force data and extension data, and then taken in the CPU 21.

In the CPU 21, among each measurement data obtainable during an examination in such a way as described above, the measurement data set in a controlled variable is fed back every second relative to a preset target value. As a result, the measurement data controls the driving device 14 in such a way as following the target value. At the same time, each item of measurement data is stored in a separate memory (not shown in the figure). The controlled variable can be set for use or nonuse of each channel in the A/D conversion IC 22, 23 and can be selected by the operation of an operating portion 2a connected to the control device 2 by an operator.

In addition, in the embodiment depicted in FIG. 2, outputs from sensors other than the load cell 16 and extensometer 17, such as for example, strainmeters 18, 19 attached to a specific location of the test piece W, or a specific jig which transforms with a test, are also digitalized. The outputs are digitalized by the A/D converter 23 after being amplified by the amplifiers 24c, 24d, and stored in the memory as test data.

Each A/D conversion IC 22, 23 is a delta/sigma-type A/D converter, and respectively includes multiple channels (for example, 3 channels), and also a digital communication function. The use/nonuse state of each channel can be set by a selection signal transmitted through the communication function, and the number of used channels and the sampling rate, or the accuracy are traded off. In other words, the greater the number of channels that is used, the longer the sampling period of each channel, or the lower the accuracy of the sampling period. Conversely, the fewer the number of channels that is used, the shorter the sampling period of each channel, or the better the accuracy of the sampling period.

More specifically, in a case in which only one channel among the three channels is used, the channel can be used at high speeds and with a high degree of accuracy. In a case in which two channels are used, the channels can be used at high speeds and with a low degree of accuracy, or at low speeds and with a high degree of accuracy. In a case in which all three channels are used, the channels can be used at low speeds and with a low degree of accuracy. The use or nonuse state of each channel is chosen by digital communication with each A/D conversion IC 22, 23 through CPU 21 by the operation of the operating portion 2a.

A test-force detection signal by the load cell 16 is input into the first channel of one A/D conversion IC 22, and an extension-detection signal by the extensometer 17 is input into the second channel, respectively. The extension-detection signal by the extensometer 17 is also input into the first channel of another A/D conversion IC 23. Also, deformation-detection signals by the strainmeters 18, 19 are input into the second channel and third channel of another A/D conversion IC 23, respectively.

In the above-mentioned structure, in a case where only output from the load cell 16 is digitalized, only the first channel of one A/D converter 22 is placed in a used state by the operation of the operating portion 2a by the operator. Herewith, the output of the load cell 16 is digitalized at high speeds and with a high degree of accuracy.

In a case where the outputs from the load cell 16 and extensometer 17 are digitalized, the first channel of one A/D conversion IC 22 and the first channel of another A/D conversion IC are placed in the used state. Herewith, each output is digitalized at high speeds and with a high degree of accuracy.

In a case where outputs from two strainmeters 18, 19 are also required to be digitalized besides the outputs from the load cell 16 and extensometer 17, the first and second channels of one A/D conversion IC 22 and the second and third channels of another A/D conversion IC 23 are placed in the used state. Herewith, each output from the load cell, 16, extensometer 17, and two strainmeters 18, 19 is digitalized at low speeds and with a high degree of accuracy, or at high speeds and with a low degree of accuracy.

Alternatively, in a case where only output from the load cell 16 is required to be digitalized at high speeds and with a high degree of accuracy, while the above-mentioned four outputs are digitalized, the first channel of one A/D conversion IC and the first, second, and third channels of the other A/D conversion IC 23 are placed in the used state. Herewith, the output from the load cell 16 is digitalized at high speeds and with a high degree of accuracy, and the outputs from the extensometer 17 and each strainmeter 18, 19 are digitalized at low speeds and with a low degree of accuracy.

A notable feature of the above-mentioned embodiment of the invention is that when each detection output is digitalized, the priority sequence of the number of the channels, sampling rate, and accuracy can be chosen by the operator. The number of channels, sampling rate, and accuracy can be set optimally according to the use conditions, such as the content of the test.

The number of the A/D conversion ICs and the number of the channels are not limited to the embodiments described herein, and instead, can be determined by a particular application of the invention. Also, the type of the detector is not limited to the embodiment described herein. In addition, besides a tensile test, the present invention is equally applicable to other tests such as a fatigue test.

The disclosure of Japanese Patent Application No. 2005-018740 filed on Jan. 26, 2005, is incorporated herein.

What is claimed is:

1. A material testing machine comprising:
   a load mechanism for applying a load to a test piece;
   a plurality of detectors for detecting physical values associated with the applied load;
   an A/D converter for receiving output measurement data of each of the detected physical values, and for digitalizing the received output data from each of the plurality of detectors, wherein the A/D converter comprises multiple channels, and can select use/nonuse of each of the multiple channels based on input from an external selection signal; and
   selective means for supplying the external selection signal to the A/D converter,
   wherein at least one of detecting rate and a detecting accuracy is inversely proportional to the number of the multiple channels that are in use.

2. A material testing machine according to claim 1, wherein the plurality of detectors is selected from the group consisting of a load cell, an extensometer, a strainmeter, and a fatigue detector.

3. A material testing machine according to claim 1, wherein the A/D converter is a delta/sigma-type integrated circuit converter.

4. A material testing machine according to claim 1, further comprising a central processing unit for receiving the digitalized output data from the A/D converter and for controlling the load applied to the test piece.

5. A material testing machine according to claim 1, wherein said at least one of the detecting rate and the detecting accuracy is greatest when the number of the multiple channels that are in use is one.

6. A material testing machine according to claim 1, further comprising a plurality of amplifiers associated with the plurality of detectors, respectively, for amplifying the output values.

7. A material testing machine comprising:
   a load mechanism for applying a load to a test piece;
   a plurality of detectors for detecting physical values associated with the applied load;
   an A/D converter for receiving output measurement data of each of the detected physical values, and for digitalizing the received output data from each of the plurality of detectors, wherein the A/D converter comprises multiple channels, and can select use/nonuse of each of the multiple channels based on input from an external selection signal; and
   selective means for supplying the external selection signal to the A/D converter,
   wherein multiple A/D converters are provided.

8. A material testing machine according to claim 7, wherein
   output of at least one detector is split and input in parallel to the channels of two of the multiple A/D converters, and
   at least one channel of each of the two A/D converters receiving the split signal is set in a used state.

* * * * *